(12) United States Patent
Peters et al.

(10) Patent No.: US 10,583,284 B2
(45) Date of Patent: Mar. 10, 2020

(54) METHODS FOR TREATING A TIBIAL NERVE-RELATED CONDITION

(71) Applicant: William Beaumont Hospital, Royal Oak, MI (US)

(72) Inventors: Kenneth M. Peters, Huntington Woods, MI (US); Larry Sirls, Bloomfield Hills, MI (US)

(73) Assignee: WILLIAM BEAUMONT HOSPITAL, Royal Oak, MI (US)

( * ) Notice: Subject to any disclaimer, the term of this patent is extended or adjusted under 35 U.S.C. 154(b) by 346 days.

(21) Appl. No.: 15/477,978

(22) Filed: Apr. 3, 2017

(65) Prior Publication Data

US 2017/0281930 A1 Oct. 5, 2017

Related U.S. Application Data

(60) Provisional application No. 62/316,638, filed on Apr. 1, 2016, provisional application No. 62/354,375, filed on Jun. 24, 2016.

(51) Int. Cl.
| | | |
|---|---|---|
| *A61N 1/05* | (2006.01) | |
| *A61N 1/372* | (2006.01) | |
| *A61N 1/36* | (2006.01) | |
| *A61B 17/34* | (2006.01) | |

(52) U.S. Cl.
CPC ........ *A61N 1/0551* (2013.01); *A61B 17/3468* (2013.01); *A61N 1/3606* (2013.01); *A61N 1/36071* (2013.01); *A61N 1/36107* (2013.01); *A61N 1/37252* (2013.01)

(58) Field of Classification Search
None
See application file for complete search history.

(56) References Cited

U.S. PATENT DOCUMENTS

| | | | |
|---|---|---|---|
| 6,735,474 B1 | 5/2004 | Loeb et al. | |
| 7,729,772 B2 * | 6/2010 | Williams | ............. A61N 1/0551 |
| | | | 607/41 |
| 8,788,045 B2 | 7/2014 | Gross et al. | |
| 9,220,897 B2 | 12/2015 | Perryman et al. | |
| 9,409,030 B2 | 8/2016 | Perryman et al. | |
| 9,861,812 B2 * | 1/2018 | Gross | ................... A61N 1/0551 |
| 2016/0023005 A1 | 1/2016 | Perryman | |

OTHER PUBLICATIONS

Edenfield, Autum L., et al. Posterior Tibial Nerve Stimulation for the Treatment of Fecal Incontinence: A Systematic Evidence Review, CME Review Article, Obstetrical and Gyneccological Survey, vol. 70, No. 5, pp. 329-341.

(Continued)

*Primary Examiner* — Carl H Layno
*Assistant Examiner* — Dacheng Xie
(74) *Attorney, Agent, or Firm* — Honigman LLP; Douglas H. Siegel

(57) ABSTRACT

Methods for placing an electrical stimulation lead at a tibial nerve in a subject, and also for treating a tibial nerve-related condition or disease in the subject. The methods include depositing the electrical stimulation lead at a tibial nerve, activating the electrical stimulation lead to modulate the tibial nerve, and thereby treating the tibial nerve-related condition or disease in the subject.

22 Claims, 11 Drawing Sheets

(56) References Cited

OTHER PUBLICATIONS

Elkattah, Rayen, M.D., et al. Percutaneous Tibial Nerve Stimulation as an Off-label Treatment of Clitoral Pain. Female Pelvic Medicine & Reconstructive Surgery, vol. 20, No. 6, Nov./Dec. 2014, 4 pages.
Gokyildiz, Sule, et al. Effects of Percutaneous Tibial Nerve Stimulation Therapy on Chronic Pelvic Pain. Gynecol Obstet Invest 2012; 73-99-105.
Iqbal, F., et la. Bilateral Transcutaneous Tibial Nerve Stimulation for Chronic Constitution. Colorectal Disease 2015 The Association of Coloproctology of Great Britain and Ireland 18, 173-178, doi:10.1111/codi,13105.
Istek, Ayse, et al. Randomized Trial of Long-Term Effects of Percutaneous Tibial Nerve Stimulation on Chronic Pelvic Pain. Arch Gynecol Obstet (2014) 290:291-298.
Kabay. Sahin, et al. Efficiency of Posterior Tibial Nerve Stimulation in Category IIIB Chronic Prostatitis/Chronic Pelvic Pain: A Sham-Controlled Comparative Study. Urol Int 2009; 83:33-38.
Musco, Stefania, et al. Percutaneous Tibial Nerve Stimulation Improves Female Sexual Function in Women with Overactive Bladder Syndrome. J Sex Med 2016;13:238-242
Peters, Kenneth M., et al. Randomized Trial of Percutaneous Tibial Nerve Stimulation Versus Sham Efficacy in the Treatment of Overactive Bladder Syndrome: Results from the Sumit Trial. The Journal of Urology, vol. 183, 1438-1443, Apr. 2010.
Van Der Pal, Floor, M.D., et al. Implant-Driven Tibial Nerve Stimulation in the Treatment of Refractory Overactive Bladder Syndrome: 12-Month Follow-Up. Neuromodulation, vol. 9, No. 2, 2006 pp. 163-171.

* cited by examiner

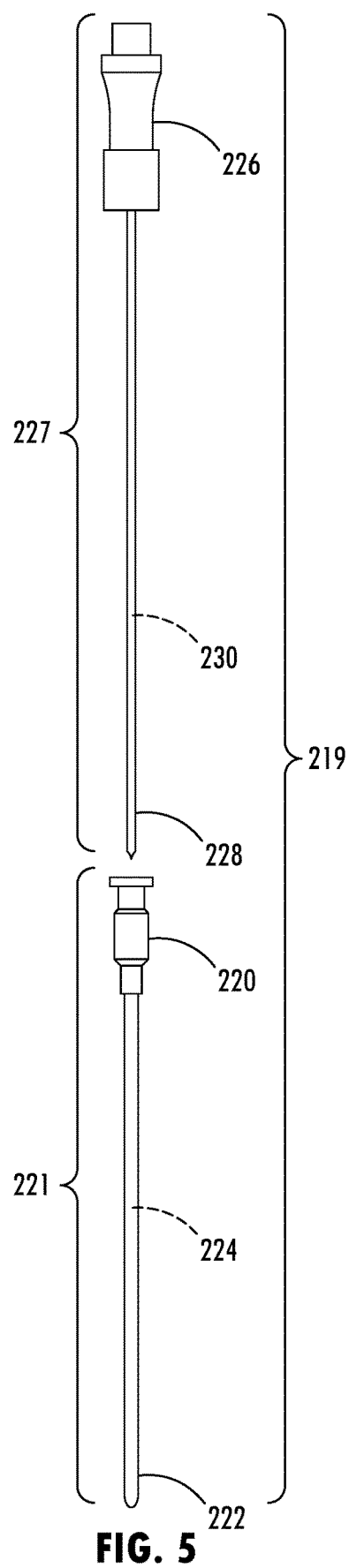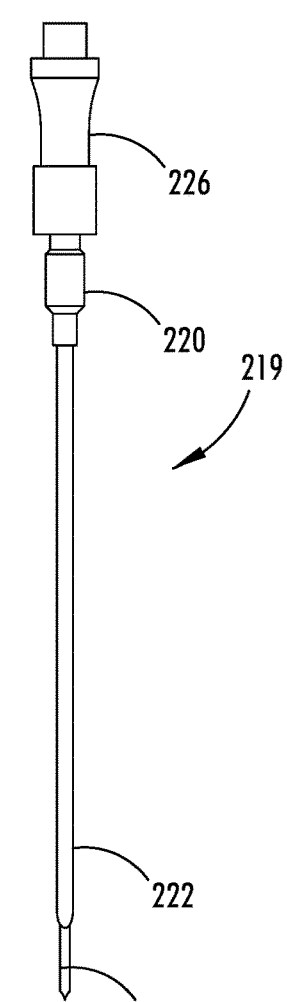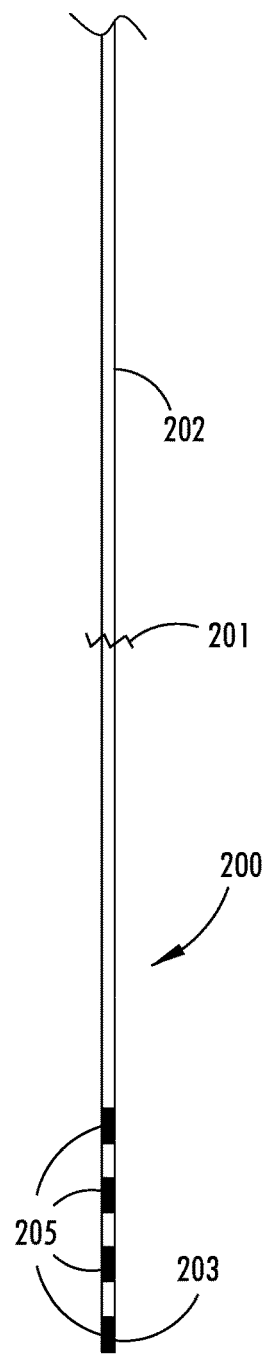
FIG. 5
FIG. 6
FIG. 7

METHODS FOR TREATING A TIBIAL NERVE-RELATED CONDITION

CROSS-REFERENCE TO RELATED APPLICATIONS

This U.S. Patent Application claims priority to U.S. Applications 62/316,638 filed on Apr. 1, 2016 and 62/354,375 filed on Jun. 24, 2016, the disclosures of which are considered part of the disclosure of this application and are hereby incorporated by reference in their entirety.

TECHNICAL FIELD

This disclosure relates to methods for treating a tibial nerve-related condition.

BACKGROUND

Modulation of the tibial nerve by electrical stimulation is an important clinical therapy for patients who suffer from a variety of tibial nerve-related conditions or diseases including chronic pain, bladder symptoms, sexual function and bowel symptoms. Current approaches to placing a lead for electrical stimulation of the tibial nerve include surgical incision and exposure of the nerve, and ante-grade percutaneous lead placement; but the current open surgical and ante-grade approaches are not ideal.

SUMMARY

This section provides a general summary of the disclosure, and is not a comprehensive disclosure of its full scope or all of its features.

One aspect of the disclosure provides a method for depositing an electrical stimulation lead at a tibial nerve in a subject, wherein the subject includes a lower leg, a knee, a foot, the tibial nerve of the lower leg, skin of the lower leg, an outside surface of the skin of the lower leg, a tibia of the lower leg, an ankle interconnecting the tibia and the foot, a medial malleolus of the ankle of the lower leg, an Achilles tendon of the lower leg, and a tibial vascular bundle of the lower leg, wherein the tibia, the tibial nerve, and the tibial vascular bundle each have a length, and wherein the tibia, the tibial nerve and the tibial vascular bundle extend along a longitudinal axis from the ankle to the knee. This method may include determining an incision site that is between the medial malleolus and the Achilles tendon of the subject; making an incision through the skin of the lower leg at the incision site; locating a portion of the length of the tibial nerve in the subject; obtaining the electrical stimulation lead; inserting the electrical stimulation lead through the incision site and subcutaneously advancing the electrical stimulation lead in a direction from the incision site toward the knee of the subject, along the longitudinal axis, and substantially along the portion of the length of the tibial nerve; and depositing the electrical stimulation lead at a final lead location that is at the tibial nerve in the subject.

In other embodiments, the electrical stimulation lead may have a proximal and a distal end and a longitudinal dimension from its proximal end to its distal end; at the final lead location, the longitudinal dimension of the electrical stimulation lead may be oriented substantially parallel to the portion of the length of the tibial nerve; and a Tibialis Posterior, a Flexor Digitorum Longus, a Flexor Hallucis Longus, and a Soleus of the subject may be located around the final lead location of the electrical stimulation lead.

In other aspects, the determining step may include palpating an area between the medial malleolus and the Achilles tendon of the subject; and the incision site may be located about one-third of the distance from the medial malleolus to the Achilles tendon of the subject.

Other steps of the inventive method may include locating a portion of the length of the tibia of the subject and marking a plurality of locations along the portion of the length of the tibia by placing a plurality of marks on the outside surface of the skin of the lower leg, at the tibia of the subject, and spaced-apart along the longitudinal axis of the tibia; the location of the plurality of marks may be a proxy for the location of the portion of the length of the tibial nerve; the electrical stimulation lead may be connected to a housing having a proximal end and a distal end and having a longitudinal dimension from its proximal end to its distal end, wherein the longitudinal dimension of the housing is longer than the longitudinal dimension of the electrical stimulation lead, and wherein the electrical stimulation lead is located toward the distal end of the housing.

More aspects of the inventive method may include one or more of obtaining a finder needle, wherein the finder needle has cannula, proximal and distal ends, and a total length, and has a predetermined length that is at least as long as the longitudinal dimension of the electrical stimulation lead, that is less than the total length of the finder needle, and that extends from the distal end toward the proximal end of the finder needle; inserting the distal end of the finder needle through the incision site; subcutaneously advancing the predetermined length of the finder needle toward a stimulation locus on the portion of the length of the tibial nerve; obtaining an electrical stimulation apparatus capable of emitting an electrical charge; connecting the electrical stimulation apparatus to the proximal end of the inserted finder needle; activating the electrical stimulation apparatus to emit an electrical charge to the finder needle; and determining that the distal end of the finder needle is at or proximate the stimulation locus if the subject shows a physiological response to the electrical charge. Optionally, the physiological response may be a motor-response in the foot or toe of the subject.

When it has been determined that the distal end of the finder needle is at or proximate the stimulation locus, the method may further include: obtaining a guide wire, wherein the guide wire has proximal and distal ends, has a total length, and has a predetermined length that is about the same as the predetermined length of the finder needle, that is less than the total length of the guide wire, and that extends from distal end of the guide wire toward its proximal end; inserting the distal end of the guide wire through cannula of the finder needle; advancing the predetermined length of the guide wire to the stimulation locus; removing the finder needle from subject; obtaining an introducer, wherein the introducer has proximal and distal ends, has a total length, and has a predetermined length that is about the same as the predetermined length of the finder needle, that is less than the total length of the introducer, and that extends from distal end of the introducer toward the proximal end of the introducer; placing the distal end of the introducer over the proximal end of the guide wire; advancing the predetermined length of the introducer to the stimulation locus; removing the guide wire from subject; inserting the distal end of the electrical stimulation lead through the introducer; advancing the electrical stimulation lead to the final lead location, wherein the final lead location is at or proximate the stimulation locus; removing the introducer from the subject; disconnecting the electrical stimulation lead from a portion of the housing to deposit the electrical stimulation lead at the final lead location; removing the disconnected portion of the housing from the subject; and suturing shut the incision.

In another aspect of the invention, the predetermined length of the finder needle may about the length of the electrical stimulation lead.

Another aspect of the step of locating the portion of the length of the tibial nerve may include determining a location of a portion of the length of the tibial vascular bundle, wherein the location of the portion of the length of the tibial vascular bundle is a proxy for the location of the portion of the length of the tibial nerve, and wherein blood flow through the tibial vascular bundle is indicative of the location of the portion of the length of the tibial vascular bundle.

Additional inventive methods may include performing one or more steps of the above-described inventive process to treat a tibial nerve-related condition or disease in a subject having the tibial nerve-related condition or disease. These treatment methods also may include obtaining an controller module, wherein the controller module is in communicable relation with the electrical stimulation lead, and wherein the controller module is activatable to cause the electrical stimulation lead to emit an electrical pulse to the tibial nerve of the subject; and activating the controller module to cause the electrical stimulation lead to emit an electrical pulse to the tibial nerve, thereby modulating the tibial nerve and treating the tibial nerve-related condition or disease in the subject. In one aspect of the treatment method, the controller module may be in wireless communication with the electrical stimulation lead.

In another embodiment, the tibial nerve-related condition or disease that is treated may be overactive bladder syndrome, urge incontinence, clitoral pain, peripheral neuropathy from dysfunction of the tibial nerve, colonic constipation, fecal or urinary incontinence, chronic pelvic pain syndrome, perineal or perianal pain, chronic prostatitis, stress incontinence, bladder pain, bladder inflammation, vesico-urethral dysfunction, genito-urinary disorders, urge frequency, urinary pain, erectile/sexual disorders, non-obstructive urinary retention, or interstitial cystitis/painful bladder syndrome.

The details of one or more implementations of the disclosure are set forth in the accompanying drawings and the description below. Other aspects, features, and advantages will be apparent from the description and drawings, and from the claims.

DESCRIPTION OF DRAWINGS

The foregoing summary, as well as the following detailed description of the invention, will be better understood when read in conjunction with the appended drawings. For the purpose of illustrating the invention, there are shown in the drawings, certain embodiment(s) which are presently preferred. It should be understood, however, that the invention is not limited to the precise arrangements and instrumentalities shown.

In FIG. 1, the lower leg muscles are terminating via the tendons creating a space or safe zone proximate the tibial nerve and tibial vascular bundle for placement of an electrical stimulation lead. The tibial nerve is between the medial malleolus of the ankle and Achilles tendon.

FIG. 2A is the cross-section that is closest to the knee. In FIG. 2A, the tibial nerve and the tibial vascular bundle are more deeply located and surrounded by the muscle bellies of the Tibialis Posterior, Flexor Digitorum Longus, Flexor Hallucis Longus, and the Soleus.

In FIG. 2B, further down the leg, the tibia is more prominent than higher up (FIG. 2A), and the muscle bellies are smaller and terminate into tendons that insert into the bones. The tendons of the Tibialis Posterior and Flexor Digitorum Longus (and not the muscle bellies) are shown.

FIG. 5 depicts an exemplary two-part introducer that may be used in the methods of the present invention, with the two parts in a disassembled condition.

FIG. 6 depicts the introducer of FIG. 5 in an assembled condition.

FIG. 7 depicts an exemplary electrical stimulation needle that may be used in the methods of the present invention.

DETAILED DESCRIPTION

Figure 1:
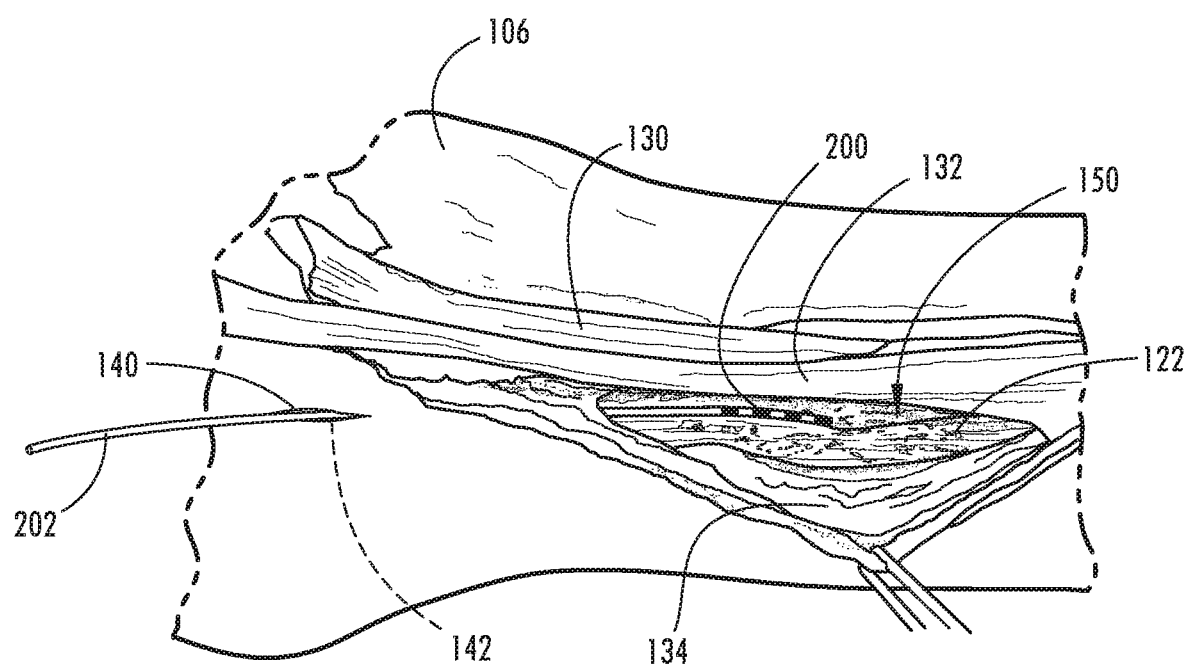
FIG. 1 depicts a dissection of a medial lower right leg and ankle of a subject and shows anatomic landmarks used in the inventive method; specifically, the medial malleolus and the Achilles tendon.
Figure 1A:
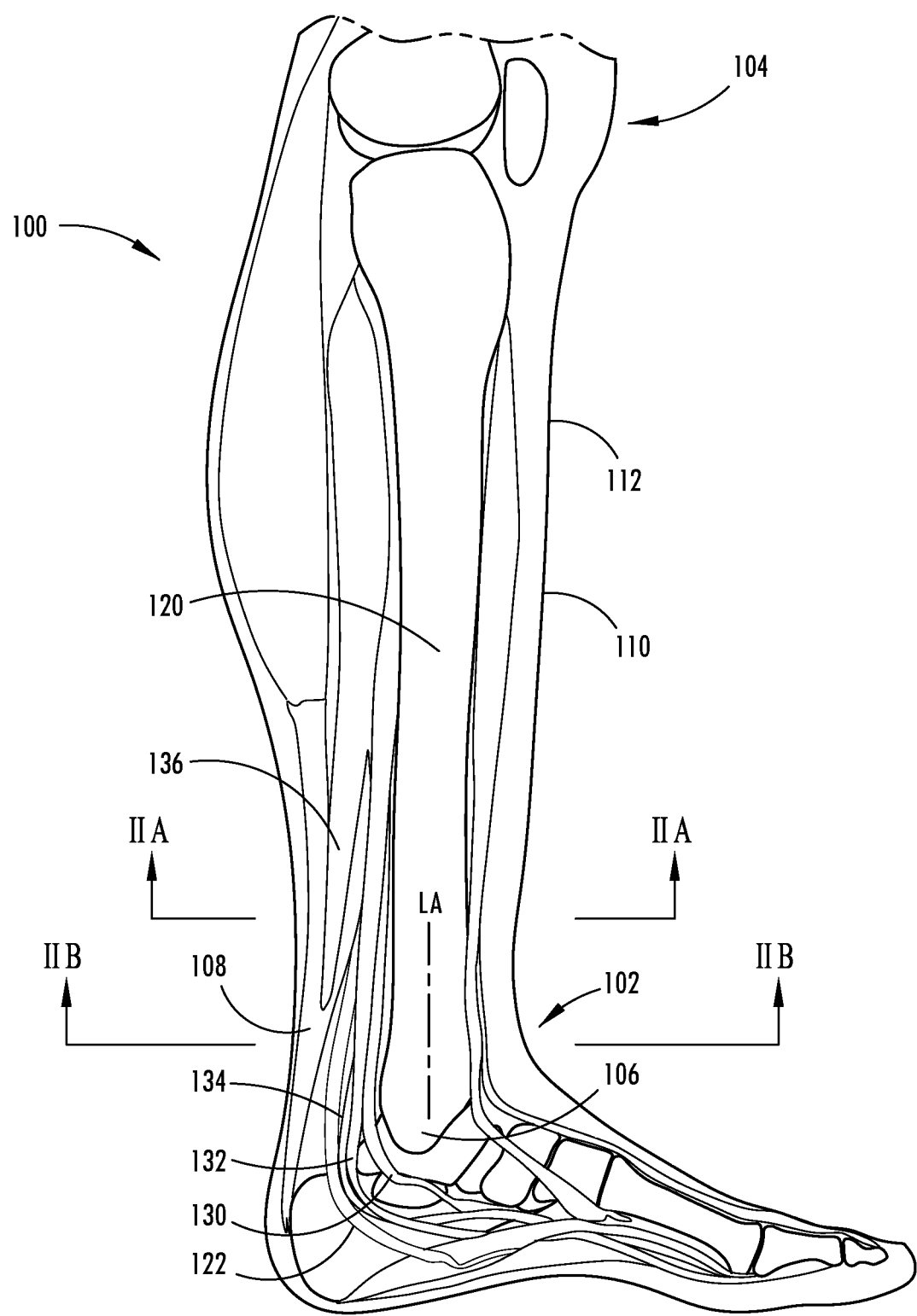
FIG. 1A depicts a cross-sectional view of a medial lower left leg, ankle and foot of a subject.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

All references, patents, patent publications, articles, and databases, referred to in this application are incorporated herein by reference in their entirety, as if each were specifically and individually incorporated herein by reference. Such patents, patent publications, articles, and databases are incorporated for the purpose of describing and disclosing the subject components of the invention that are described in those patents, patent publications, articles, and databases, which components might be used in connection with the presently described invention. The information provided below is not admitted to be prior art to the present invention, but is provided solely to assist the understanding of the reader.

The details of one or more embodiments of the invention are set forth in the accompanying drawings and the description below. Other features, embodiments, and advantages of the invention will be apparent from the description and drawings, and from the claims. The preferred embodiments of the present invention may be understood more readily by reference to the following detailed description of the specific embodiments and the Examples included hereafter.

Unless defined otherwise, all technical and scientific terms used herein have the meaning commonly understood by one of ordinary skill in the art to which this invention belongs. Although any methods, devices and materials similar or equivalent to those described herein can be used in the practice or testing of the invention, the inventive methods, devices and materials are now described.

Definitions

The terminology used herein is for the purpose of describing particular exemplary configurations only and is not intended to be limiting. As used herein, the singular articles "a," "an," and "the" may be intended to include the plural forms as well, unless the context clearly indicates otherwise. The terms "comprises," "comprising," "including," and "having," are inclusive and therefore specify the presence of features, steps, operations, elements, and/or components, but do not preclude the presence or addition of one or more other features, steps, operations, elements, components, and/or groups thereof. The method steps, processes, and operations described herein are not to be construed as necessarily requiring their performance in the particular order discussed or illustrated, unless specifically identified as an order of performance. Additional or alternative steps may be employed.

When an element or layer is referred to as being "on," "engaged to," "connected to," "attached to," or "coupled to" another element or layer, it may be directly on, engaged, connected, attached, or coupled to the other element or layer, or intervening elements or layers may be present. In contrast, when an element is referred to as being "directly on," "directly engaged to," "directly connected to," "directly attached to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The term "at a tibial nerve" as used herein generally refers to a location that is directly or indirectly in contact with the tibial nerve, and includes locations that are proximate to the tibial nerve.

The term "locus" as used herein refers to a positional location or site; here, for example a positional location or site of the tibial nerve.

The term "medical practitioner" as used herein refers to a physician, or other person who is qualified and/or certified to perform a medical procedure on a subject.

The terms "palpate" or "palpating" generally refer to touching for medical purposes, for example, touching an area between the medial malleolus of the ankle and the Achilles tendon to determine the location for the incision site.

The term "predetermined" as used herein means established or decided in advance of an occurrence or event. For example, establishing the length of a component or part before its use.

The term "proximate to" as used herein generally refers to a location that is next to, nearest to, adjacent to, and/or immediately before or after another location.

The term "proxy" as used herein refers to a substitute for or approximation of something else.

The terms "subcutaneous" or "subcutaneously" as used herein generally means under the skin or moving in a direction under the skin; and the terms "percutaneous" or "percutaneously" as used herein generally means through the skin or moving in a direction through the skin.

The term "subject" or "patient" as used herein generally refers to any living organism to and may include, but is not limited to, any human, primate, or non-human mammal in need of diagnosis and/or treatment for a condition, disorder or disease (e.g., chronic pain). A "subject" may or may not be exhibiting the signs, symptoms, or pathology of the condition, disorder or disease at any stage of any embodiment.

The terms "substantially" and "about" as used herein generally refer to the inherent degree of uncertainty that may be attributed to a comparison, value, measurement, or other representation. These terms are also utilized herein to represent the degree by which a comparison, value, measurement, or other representation may vary from a stated reference without resulting in a change in the basic function of the subject matter at issue. Unless otherwise defined herein, the terms "substantially" and "about" mean that the comparison, value, measurement, or other representation may fall within 20% of the stated reference.

The term "tibial nerve-related condition or disease" as used herein refers to a medical condition or disease in which an amelioration of or cure for the condition or disease is known or suspected to be associated with medical care directed to the tibial nerve; and this term also includes a condition or disease in which the tibial nerve is known or suspected to be a cause of the condition or disease. Some examples of a tibial nerve-related condition or disease include but are not limited to overactive bladder syndrome (often associated with detrusor muscle overactivity), urge incontinence, clitoral pain, peripheral neuropathy (nerve pain) from dysfunction of the tibial nerve, colonic constipation, fecal or urinary incontinence, chronic pelvic pain syndrome (localized in the pelvis, infraumbilical anterior abdominal wall, or lumbosacral back or buttocks, groin, bladder, genitals, lower abdomen), perineal or perianal pain, chronic prostatitis, stress incontinence, bladder pain, bladder inflammation, vesico-urethral dysfunction, genito-urinary disorders, urge frequency, urinary pain, erectile/sexual disorders, non-obstructive urinary retention, and interstitial cystitis/painful bladder syndrome.

The terms "Tibialis Posterior", "Flexor Digitorum Longus", "Flexor Hallucis Longus", and "Soleus," as used herein refer to muscles in the lower leg of a subject and, include both the muscle belly and the tendon extending from the muscle belly for each of these anatomical parts.

The term "treating" as used herein refers to the prophylaxis of a specific disorder, disease, or condition, alleviation of the symptoms associated with a specific disorder, disease, or condition and/or prevention of the symptoms associated with a specific disorder, disease or condition. In some embodiments, the term refers to slowing the progression of the disorder, disease, or condition or alleviating the symptoms associated with the specific disorder, disease, or condition. In some embodiments, the term refers to restoring function which was impaired or lost due to a specific disorder, disease, or condition.

The meanings of the anatomical terms used herein, such as, lower leg, knee, foot, tibial nerve, skin, outside surface of the skin, fascia, tibia, ankle, medial malleolus, Achilles tendon, and tibial vascular bundle are common anatomical terms and their meanings (e.g., tissue type, size, locations independently and relative to each other, and function) are well-known and understood by medical practitioners and those skilled in the medical sciences.

Because of the differing sizes of subjects, the sizes of the various parts of the anatomy described herein differ from subject to subject. However, the relative sizing of the anatomical parts in a subject, each part to another, in one subject generally is about the same as the relative sizing of the anatomical parts, each part to another, in another subject.

The terms first, second, third, etc. may be used herein to describe various elements, components, regions, layers and/or sections. These elements, components, regions, layers and/or sections should not be limited by these terms. These terms may be only used to distinguish one element, component, region, layer or section from another region, layer or section. Terms such as "first," "second," and other numerical terms do not imply a sequence or order unless clearly indicated by the context. Thus, a first element, component, region, layer or section discussed below could be termed a second element, component, region, layer or section without departing from the teachings of the example configurations.

The present invention generally is directed to a method of placing an electrical stimulation lead at a tibial nerve in a subject, and also to providing treatment for a tibial nerve-related condition or disease in the subject by depositing of an electrical stimulation lead at a tibial nerve, the activation of the electrical stimulation lead and resulting modulation of the tibial nerve and treatment of the tibial nerve-related condition or disease in the subject. The tibial nerve is a branch of the sciatic nerve that passes alongside the tibia and into the foot.

Certain apparatuses and devices for modulating the tibial nerve of a subject currently are generally known, some of which are disclosed in U.S. Pat. Nos. 9,220,897 and 9,409,030 and in US Patent Publication US2016/0023005 to Micron Devices LLC. As some of those apparatuses and devices may be used in practicing the present methods, the disclosures of the materials, dimensions, functions and operations of those apparatuses and devices as disclosed in those references are incorporated herein by reference.

Figure 20:
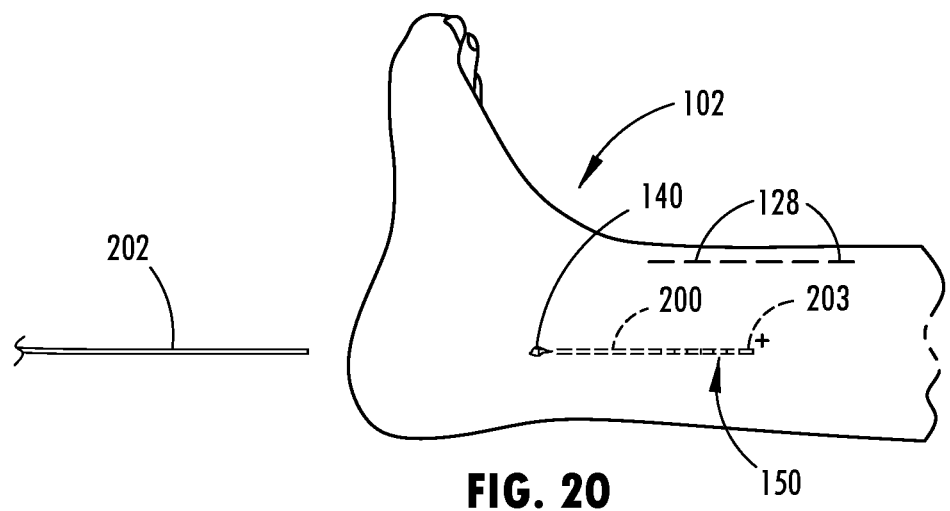
Figure 21:
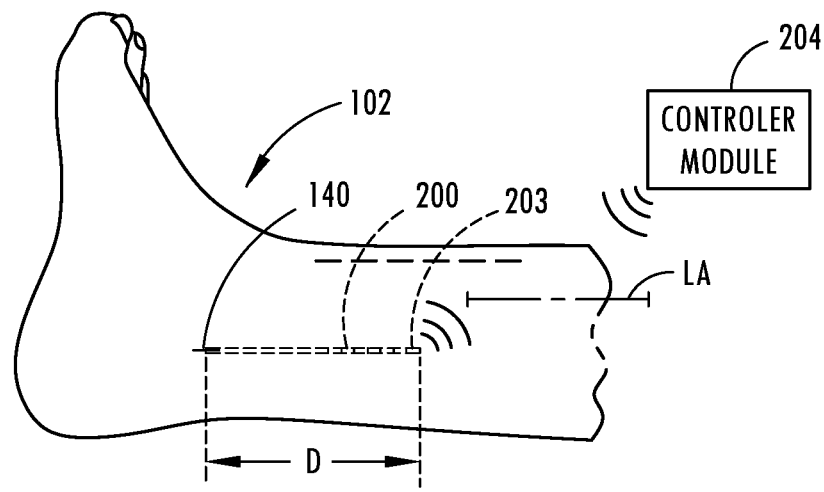

The equipment that may be used to practice the present invention may include an external controller module 204 and an implantable wireless electrical stimulation lead 200 that is connected to a housing 202 (FIGS. 20 and 21). In one embodiment, the electrical stimulation lead 200 is contained within the housing 202. The housing 202 of the electrical stimulation lead 200 may have a length of from about 1 cm to about 40 cm, or from about 5 cm to about 15 cm.

In another embodiment the electrical stimulation lead 200 may include functional components, such as, electrodes 205 (FIG. 7), circuitry, wires, and an antenna (not shown) for receiving an input signal from the controller module. The electrical stimulation lead 200 may be any one of a curved electrical stimulation lead, a straight electrical stimulation lead, a leaded electrical stimulation lead, a non-leaded electrical stimulation lead, a flanged electrical stimulation lead, and a tined electrical stimulation lead. In one embodiment, the electrical stimulation lead 200 does not include an internal power source. The circuitry of the electrical stimulation lead 200 may include only passive components. The input signal may have a carrier frequency in the range from about 300 MHz to about 8 GHz The controller module 204 may include circuitry, a power source and a transmitting antenna (not shown) for transmitting the input signal via radiative electronic coupling to the antenna of the electronic stimulation device. The controller module 204 may be loaded with programs to provide control of pulse amplitude, pulse width, frequency, ON time and OFF time of electrical pulses applied by the electrodes on the electronic stimulation lead. A medical practitioner and/or patient may determine the particular program for therapy for effective relief of the tibial nerve-related condition or disease. Once the program is determined, the controller module 204 may send an input signal via a radio frequency carrier signal to the antenna in the electronic stimulation lead 200 and the antenna and internal circuitry on electronic stimulation lead 200 may then convert this input signal to electrical pulses. The electrical pulses may be applied to the electrodes 205 within the electronic stimulation lead 200 to modulate the tibial nerve.

The electronic stimulation lead 200 may have a distal end 203 and a proximal end. In one embodiment, the functional components of the electrical stimulation lead 200, including the electrodes 205, may collectively be located at the distal end of the electronic stimulation lead 200. The electronic stimulation lead 200 may have between one and twenty-four cylindrical electrodes 205 with a diameter between about 0.1 mm and about 0.8 mm. The diameters and other dimensions of the electrodes 205 may differ depending of the particular application, course of treatment, and condition or disease being treated.

In some embodiments, one or more other pieces of medical equipment (other than the electrical stimulation lead 200 and the controller module 204) may be used in practice of the present invention; and their uses will be described below. As shown in FIGS. 3-7 (and also FIGS. 8-19), the other medical equipment may include at least four other pieces, as follows: (1) an electrical stimulation apparatus (not shown) including a hook electrode 206; (2) a finder needle 208, including a proximal end 210, a distal end 212, a cannula 214 therethrough, and a shaft and tip (not shown); (3) a guide wire 215, including a proximal end 216 and a distal end 218; and (4) an introducer 219, including an external component 221 (having a proximal end 220, an internal end 222, and a thin-walled cannula 224 therethrough), and an internal component 227 (also known as a "dilator," and having a proximal end 226, an distal end 228, and a thin-walled cannula 230 therethrough). These four pieces of medical equipment also are known in the art.

Each of the finder needle 208, the guide wire 215, and the internal component 227 of the introducer 219 are made of a type of metal, metal composite, or a comparably hard material and each has a diameter; and in some embodiments these diameters may range from about 5 Gauge to about 25 Gauge. In some embodiments, the external component 221 of the introducer 219 has a diameter, may be made from a stiff plastic material, or the like; and the diameter may be from about 0.05 inches to about 0.10 inches. Also, the shaft of the finder needle may be coated with an insulated material.

As will become apparent from some of the embodiments of the inventive methods described below, the guide wire may have a diameter that is less than the diameters of any of the finder needle 208, the external component 221 of the introducer 219, and the internal component 227 of the introducer 219. That is, the diameter of the guide wire is small enough so that the guide wire can passed completely through cannulas 214, 224, and 230. The diameter of the internal component 227 of introducer 219 is small enough so that the internal component 227 of introducer 219 may be fit into cannula 224 of external component 221 of introducer 219. In one embodiment the diameter of the finder needle is 20 Gauge, the diameter or the guide wire is 23 Gauge, the diameter of the internal component 227 of introducer 219 is 16 Gauge, and the diameter of the external component 221 of the introducer 219 is 0.071 inches (about the equivalent measure as 13 Gauge).

Figure 2A:
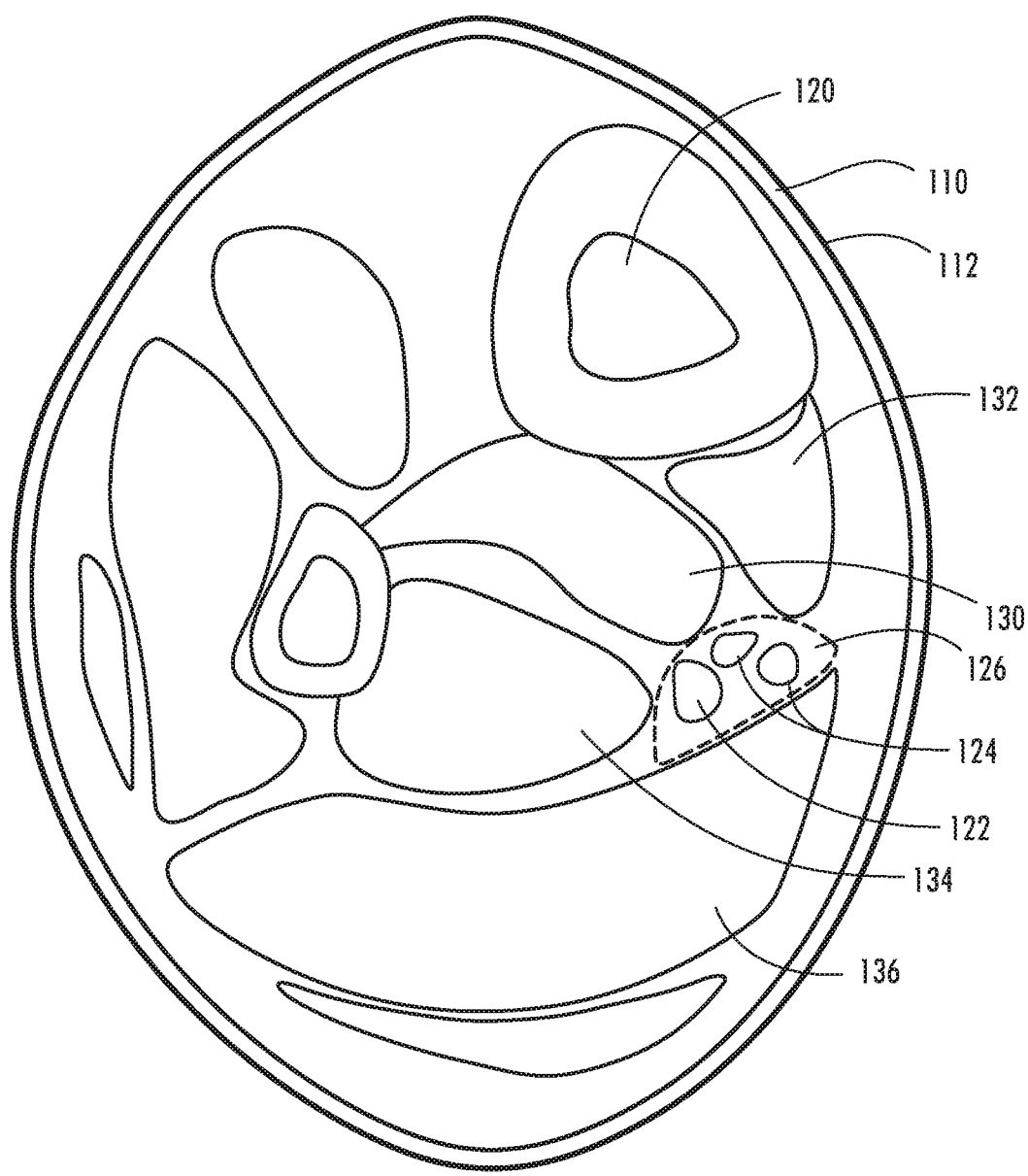
FIGS. 2A-2B are cross-sectional views that show the left lower leg taken at IIA-IIA, and IIB-IIB, respectively of FIG. 1A from the distal leg down towards the ankle, respectively.
Figure 2B:
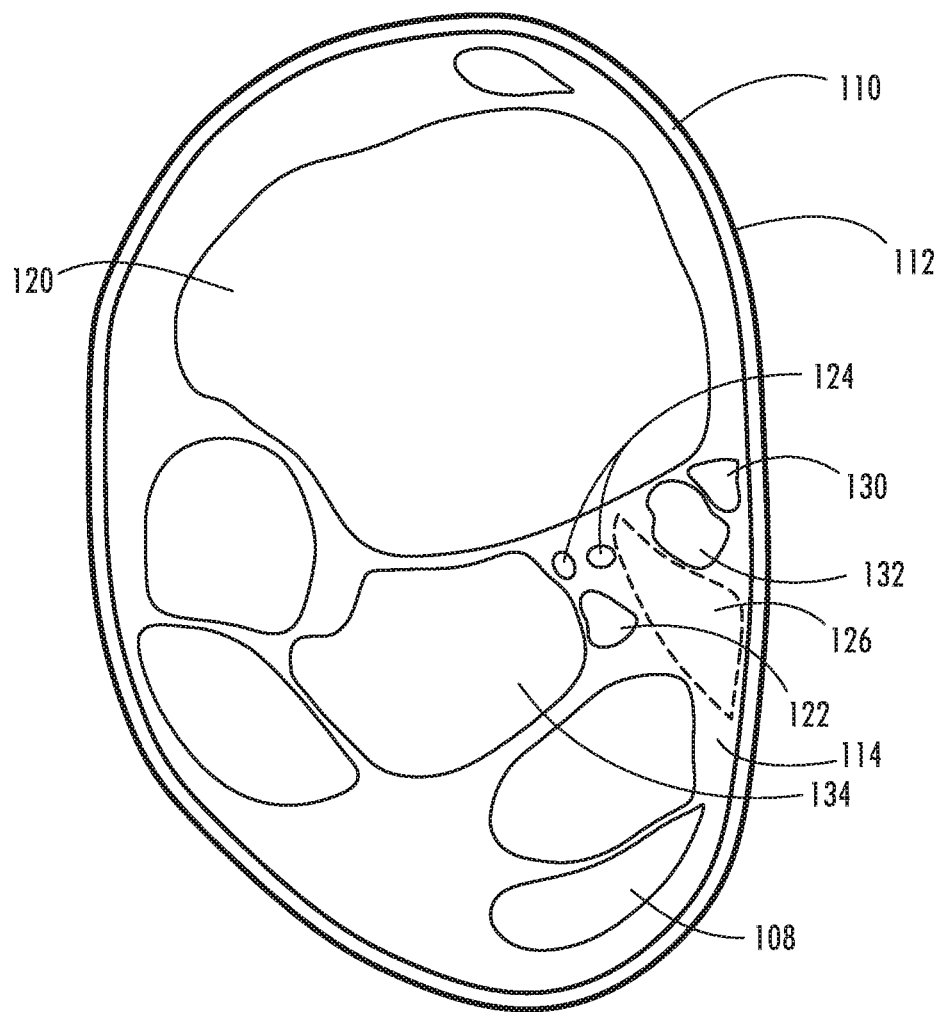
Figure 3:
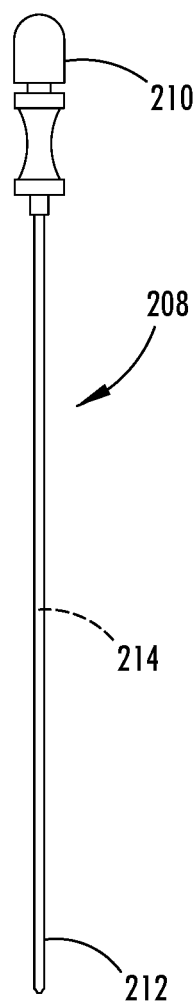
FIG. 3 depicts an exemplary finder needle that may be used in the methods of the present invention.
Figure 4:
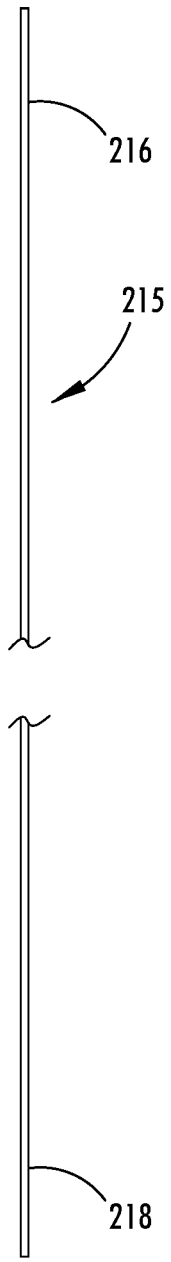
FIG. 4 depicts an exemplary guide wire that may be used in the methods of the present invention.

The methods of the present invention may be performed on a subject, for, example, a human. According to the practices of these methods, the above-described medical equipment, apparatuses and devices may be utilized in relation to the leg of a human, in particular, a lower leg 100, having an ankle 102, a knee 104, a foot 105, a medial malleolus 106 of the ankle 102, an Achilles tendon 108, skin 110 of the lower leg 100 including an outside surface 112 of the skin 110 of the lower leg 100, fascia (not shown) beneath the skin 110 of the lower leg 100, connective tissue 114, a tibia 120, a tibial nerve 122, a tibial vascular bundle 124, and muscles of lower leg 110 (Tibialis Posterior 130, Flexor Digitorum Longus 132, Flexor Hallucis Longus 134, and Soleus 136). These parts of the anatomy are shown in FIGS. 1, 1A, and 2A-2B. A tendon extends from each of the lower leg muscles 130, 132, 134, and 136 extends into a tendon. As will be discussed below, and as shown in FIGS. 2A and 2B, the inventive methods utilize a space or safe zone 126 in the lower leg 100 both to advance the electrical stimulation lead 200 from the ankle 102 toward the knee 104 of the subject and for conveniently, safely, and comfortably placing or depositing of the electrical stimulation lead 200 at a final lead location 150 in the lower leg 100. The space or safe zone 26 is proximate the tibial nerve 122 and the tibial vascular bundle 124 and the lower leg muscles Tibialis Posterior 130, Flexor Digitorum Longus 132, Flexor Hallucis Longus 134, and Soleus 136, or their corresponding tendons, are located around the final lead location 150.

In one embodiment, the inventive method may include depositing electrical stimulation lead 200 at tibial nerve 122 in a subject. The subject may be placed in a supine position, with the medical practitioner having access to the medial lower leg 100 at the foot 105/ankle 102 (the lower leg 100 then may have some degree of lateral rotation for improved access to the medial malleolus 106).

As shown in FIGS. 1 and 10-21, in one aspect the method includes the steps: determining an incision site 140 (FIG. 1) that is between the medial malleolus 106 and the Achilles tendon 108 of the subject; making an incision through the skin 110 of the lower leg 100 at the incision site 140; puncturing the fascia beneath the skin 110 to create a percutaneous opening into the space or safe zone 26; locating a portion of the length of the tibial nerve 122 in the subject; obtaining an electrical stimulation lead 200; inserting the electrical stimulation 200 lead through the incision site 140 and subcutaneously advancing the electrical stimulation lead 200 through the connective tissue 114 in a (retrograde) direction from the incision site 140 toward the knee 104 of the subject, along a longitudinal axis LA that extends from the ankle 102 to the knee 104 (FIGS. 1A and 21), and substantially along the portion of the length of the tibial nerve 122. The electrical stimulation lead 200 may be inserted into the incision site 140, subcutaneously advanced through the connective tissue 114 in a (retrograde) direction from the incision site 140 toward the knee 104 of the subject, along the longitudinal axis LA that extends from the ankle 102 to the knee 104 (FIGS. 1A and 21), and substantially along the portion of the length of the tibial nerve 122, without piercing or cutting through the muscle bellies or tendons of the Tibialis Posterior, the Flexor Digitorum Longus, the Flexor Hallucis Longus, or the Soleus of the lower leg. The electrical stimulation lead 200 then may be deposited at a final lead location 150 that is at the tibial nerve 122 in the subject. A portion of the length of the tibial nerve 122 may be a length of the tibial nerve 122 that is less than the entire length of the tibial nerve 12.

As shown in FIGS. 3-21, the electrical stimulation lead 200 may have a proximal end and a distal end 203 and a longitudinal dimension D from its proximal end to its distal end 203. At the final lead location 150, the longitudinal dimension D of the electrical stimulation lead 200 is oriented substantially parallel to the longitudinal axis LA that extends from the ankle 102 to the knee 104. In another aspect, the Tibialis Posterior, the Flexor Digitorum Longus, the Flexor Hallucis Longus, and the Soleus of the subject, or their corresponding tendons, may be located around or surrounding the electrical stimulation lead 200 at the final lead location 150.

In a further embodiment, a medical practitioner may determine the location of the incision site 140 by palpating an area between the medial malleolus 106 and the Achilles tendon 108 of the subject, for example, palpating from the most prominent, palpable portion of the medial malleolus 106 to the most palpable portion of the Achilles tendon 108. Further, the incision site 140 may be located about one-third of the distance from the medial malleolus 106 to the Achilles tendon 108. The distance between the prominent portion of the medial malleolus 106 and the edge of the Achilles tendon 108 is about 4-9 cm, with one-third of this distance being about 2-3 cm. Once located, the incision site 140 is the point-of-entry to the space or safe zone 126.

Additionally, the step of locating the portion of the length of the tibial nerve 122 may include locating a portion of the length of the tibia 120 of the subject and marking a plurality of locations along the portion of the length of the tibia by placing a plurality of marks 128 on the outside surface 112 of the skin 110 of the lower leg 100 at the tibia 120 of the subject, which marks are spaced-apart along the longitudinal axis LA; and the location of the plurality of marks 128 is a proxy for the location of the portion of the length of the tibial nerve 122. Marks 128 may visually assist the medical practitioner to subcutaneously advance the electrical stimulation lead 200 along the longitudinal axis LA through the connective tissue 114 from the incision site 140 toward the knee 104.

Alternatively, the step of locating the portion of the length of the tibial nerve 122 may include determining a location of a portion of the length of the tibial vascular bundle 124, wherein the location of the portion of the length of the tibial vascular bundle 124 is a proxy for the location of the portion of the length of the tibial nerve 122. With this alternative method, an ultrasound may be used to detect the blood flow through the tibial vascular bundle 124, and this blood flow is indicative of the location of the portion of the length of the tibial vascular bundle 124.

In one embodiment, the electrical stimulation lead 200 may be connected to a housing 202 having a proximal end and distal end 203 and having a longitudinal dimension from its proximal end to its distal end 203. The longitudinal dimension of the housing 202 is longer than the longitudinal dimension of the electrical stimulation lead 200, and the electrical stimulation lead 200 is located toward the distal end 203 of the housing.

As noted above, in some embodiments, one or more pieces of medical equipment (in addition to the electrical stimulation lead 200) may be used to practice the present invention. This other medical equipment may include one of more of the electrical stimulation apparatus (not shown) including a hook electrode 206; the finder needle 208; the guide wire 215, and the introducer 219. The finder needle 208 has a total length, and has a predetermined length that is at least as long as the longitudinal dimension D of the electrical stimulation lead 200, that is less than the total length of the finder needle 208, and that extends from the distal end 212 toward the proximal end 210 of the finder needle 28. The guide wire 215 has a total length, and has a predetermined length that is about the same as the predetermined length of the finder needle 208, that is less than the total length of the guide wire 215, and that extends from distal end 218 of the guide wire 215 toward its proximal end 216. The introducer 219, has a total length, and has a predetermined length that is about the same as the predetermined length of the finder needle 208, that is less than the total length of the introducer 219, and that extends from the distal end 228 of the internal component 227 of introducer 219 toward the proximal end 226 of the internal component 227 of introducer 219. The predetermined length of the finder needle 208 may be about the length of the electrical stimulation lead 200.

Figure 8:
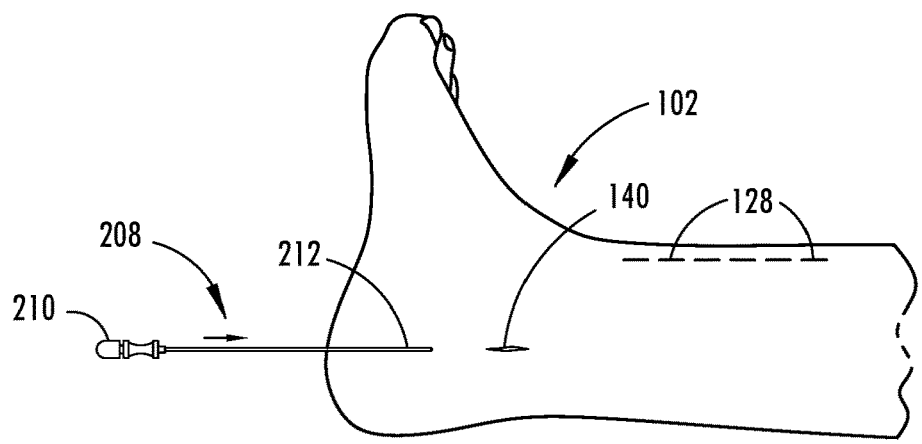
FIGS. 8-21 depict some exemplary implementations of the methods of the present invention on the medial right foot as more described hereinbelow
Figure 9:
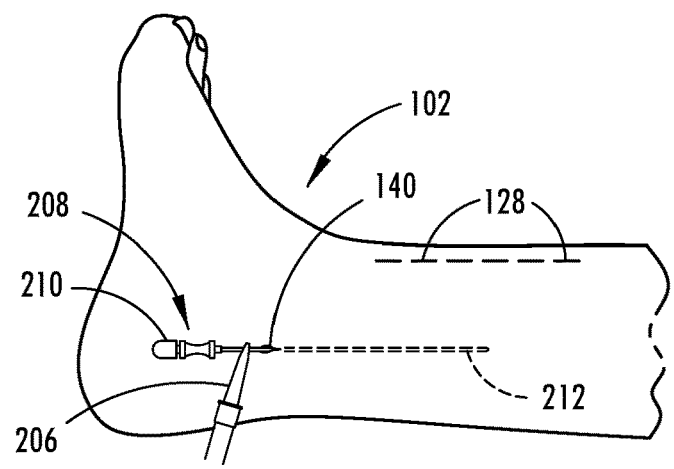

As shown in FIG. 8, in one embodiment, a medical practitioner may insert the distal end 212 of the finder needle 208 through the incision site 140 and subcutaneously advance the predetermined length of the finder needle 208. The finder needle 122 is subcutaneously advanced toward a stimulation locus (+) on the portion of the length of the tibial nerve 122 and in order to locate the stimulation locus (+) on the portion of the length of the tibial nerve 122. In a further step, the medical practitioner may use an electrical stimulation apparatus that is capable of emitting an electrical current; connecting a hook electrode 206, of the like, of the electrical stimulation apparatus (FIG. 9) to the proximal end 210 of the inserted finder needle 208; activating the electrical stimulation apparatus to emit an electrical current (e.g., a current from about 1-50 milliamperes) to the finder needle 208; and determining that the distal end 212 of the finder needle 208 is at or proximate the stimulation locus (+) if the subject shows an involuntary physiological response to the electrical charge. In one example, the physiological response of the subject is a motor-response in the foot 105 or toe of the subject. In one aspect, if the distal end 212 of the finder needle 208 is at or proximate the stimulation locus (+), the subject will involuntarily curl his or her toes.

Figure 10:
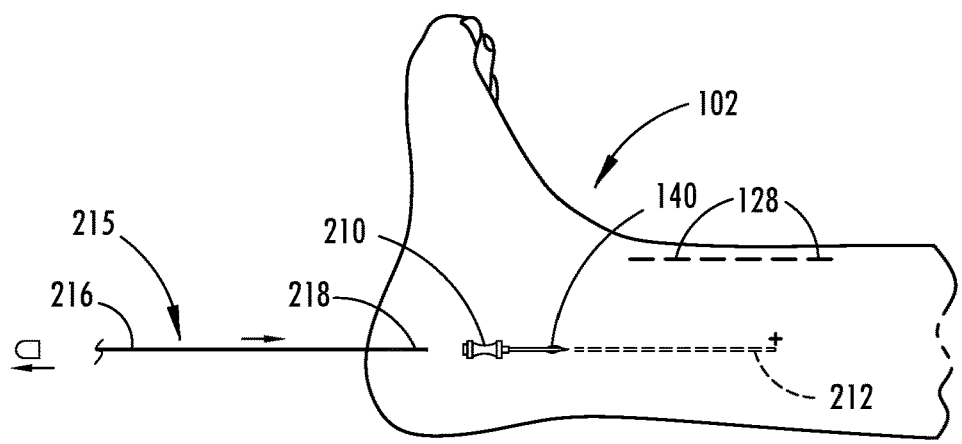
Figure 11:
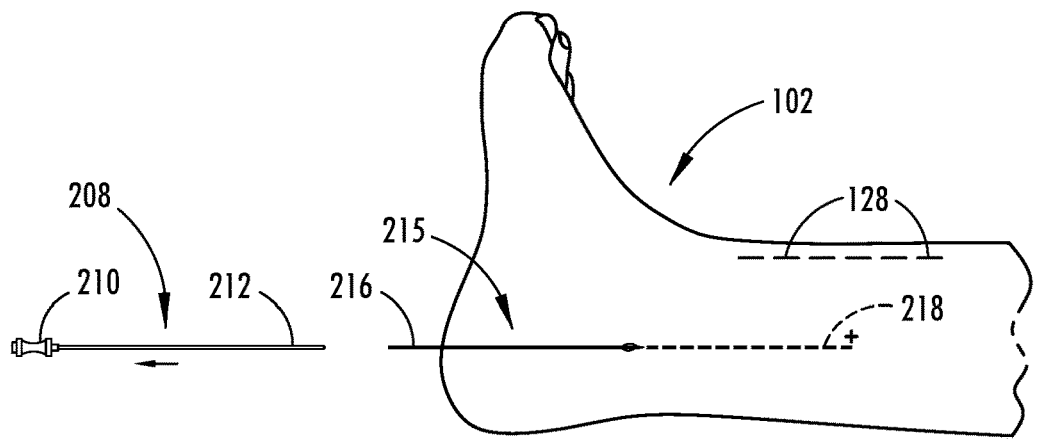

Further, if the distal end 212 of the finder needle 208 is at or proximate the stimulation locus (+), then the medical practitioner may obtain a guide wire 215. As shown in FIG. 10, the medical practitioner may insert the distal end 218 of the guide wire 215 through cannula 214 of the finder needle 208; advancing the predetermined length of the guide wire 215 to the stimulation locus (+); and then removing the finder needle 208 from subject (FIG. 11).

Figure 12:
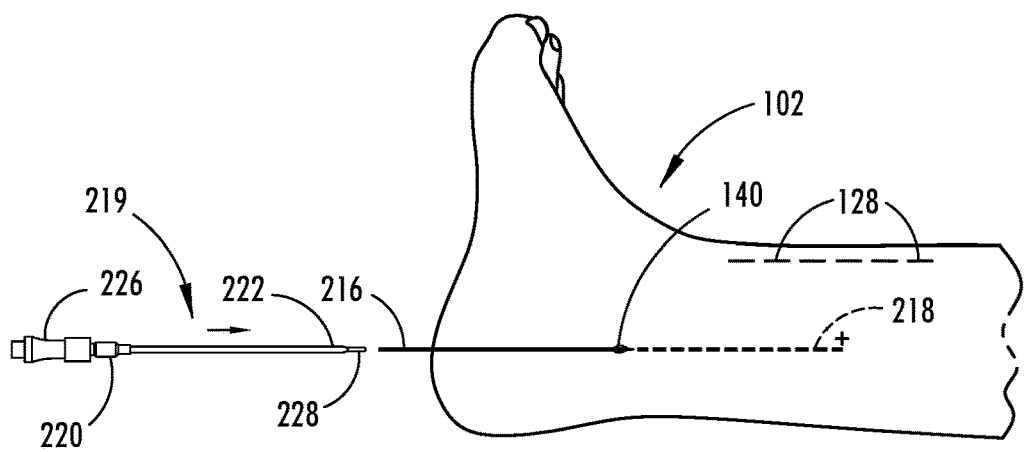
Figure 13:
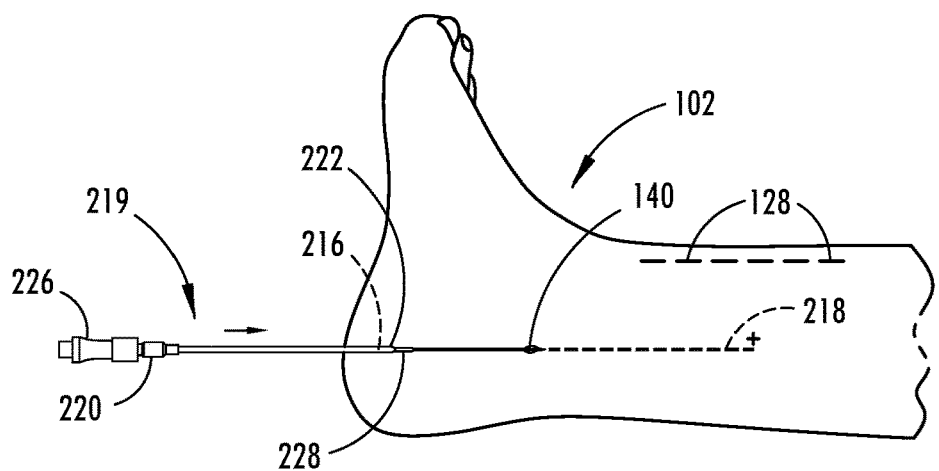
Figure 14:
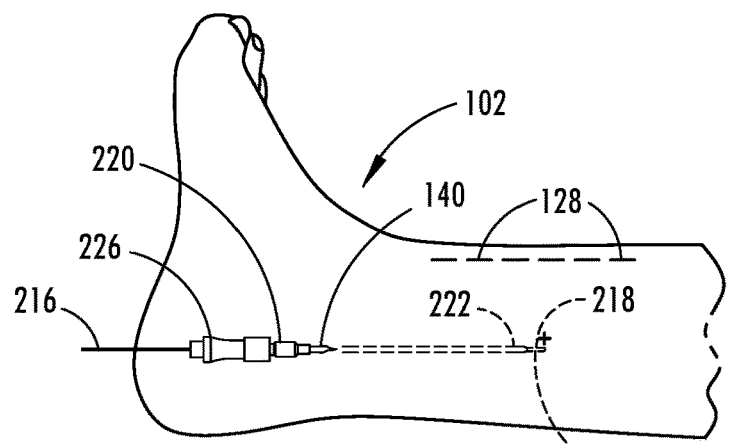
Figure 15:
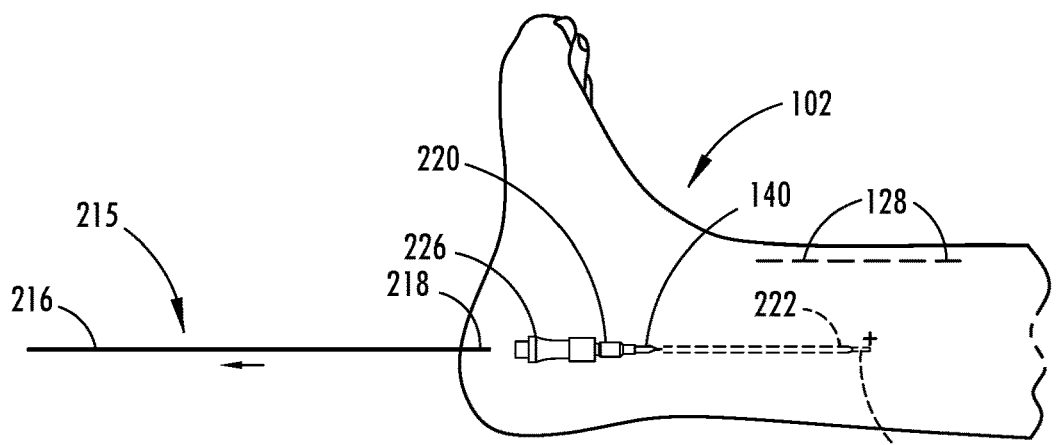
Figure 16:
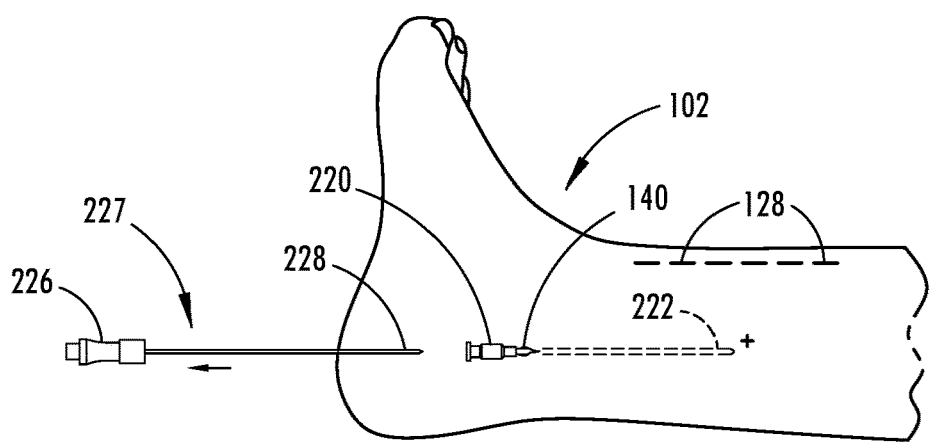
Figure 17:
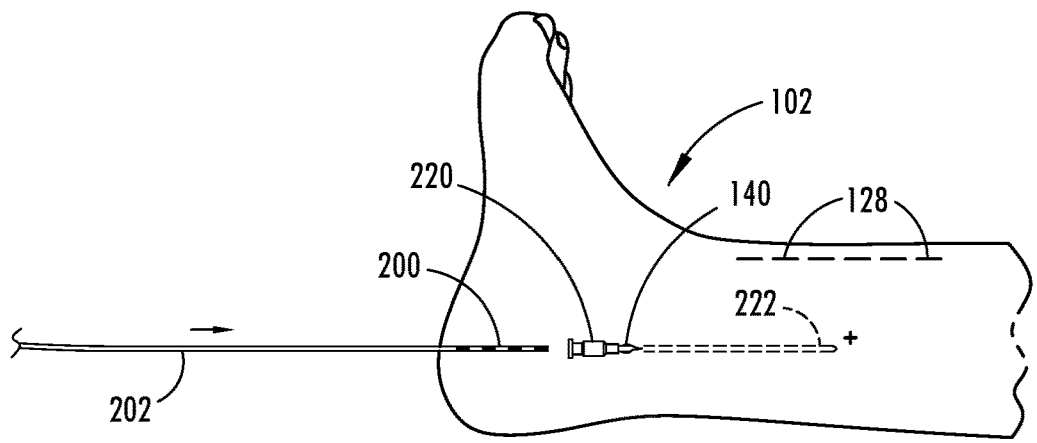

As shown in FIGS. 12 and 13, the medical practitioner further may obtain an assembled introducer 219 (i.e., the internal component 227 of the introducer 219 is fit inside of the external component 221 of the introducer 219), and may place the cannula 230 of the internal component 227 at its the distal end 228 over the proximal end 216 of the guide wire 215. As shown in FIG. 14, the medical practitioner then may advance the predetermined length of the introducer 219 to the stimulation locus (+); and then remove both the guide wire 215 (FIG. 15) and the internal component 227 of the introducer 219 (FIG. 16) from subject.

Figure 18:
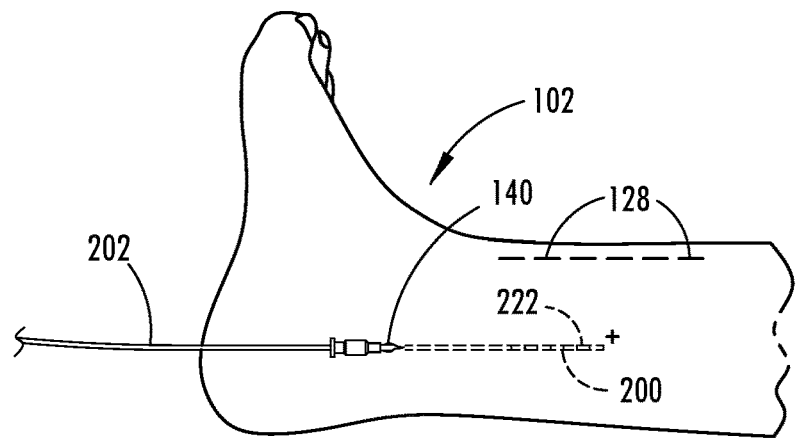
Figure 19:
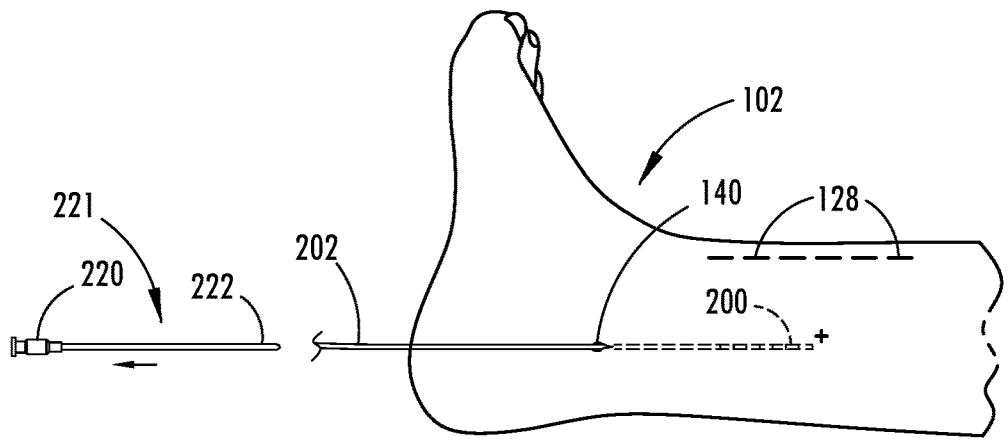

In a further aspect, the medical practitioner may insert the distal end 203 of the electrical stimulation lead 200 through the external component 221 of the introducer 219 that remains in the subject (FIG. 17); advancing the electrical stimulation lead 200 through connective tissue 114 to the final lead location 150 proximate the stimulation locus (+) (FIG. 18). The final lead location 150 may be at or proximate the stimulation locus (+). As shown in FIG. 19, the medical practitioner then may remove the external component 221 of the introducer 219 from the subject.

In another aspect of the inventive method, as shown in FIGS. 20 and 21, the medical practitioner may disconnect (e.g., cut off) the electrical stimulation lead 200 from a portion 201 of the housing 202, leaving the electrical stimulation lead 200 at the final lead location 150; and then may discard the disconnected portion 201 of the housing 202. The medical practitioner may use a permanent suture to connect the electrical stimulation lead 200 under the skin 110 at the incision site 140 (for later identification and removal of the electrical stimulation device 200). The medical practitioner then may suture shut the incision at the incision site 140.

In another embodiment of the inventive method, the incision site 140 is located between the medial malleolus 106 and the Achilles tendon 108 of the subject, the space or safe zone 126 is used by the medical practitioner for advancing the electrical stimulation lead 200 toward the knee 104, and the electrical stimulation lead 200 is deposited at the final lead location 150. Also, the tibial nerve 122 may be located by marking the tibia 120 with marks 128 (as described above), and the marks 128 may be used as a guide (or proxy for the tibial nerve 122) to advance the electrical stimulation lead in a direction from the incision site 140 toward the knee 104 of the subject, along the longitudinal axis LA, and substantially along a portion of the length of the tibial nerve 122.

In another example, the internal component 227 of the introducer 219 may be formed from a metal or other conductive material; the introducer 219 may be inserted into the incision site 140 and toward the tibial nerve 122; the hook electrode 206 of the electrical stimulation apparatus may be connected to the proximal end 226 of the internal component 227 of the introducer 219; the electrical stimulation apparatus may be activated to emit an electrical current to the distal end 228 of the internal component 227 of the introducer 219; and it may be determined that the distal end 228 of the internal component 227 of the introducer 219 is at or proximate the stimulation locus (+) of the subject upon a physiological response from the foot 105 or toe of the subject. If the distal end 228 of the internal component 227 of the introducer 219 is at or proximate the stimulation locus (+), then the medical practitioner may remove the internal component 227 of the introducer 219 from subject, leaving the external component 221 of the introducer 219 in the subject. In a further aspect, the medical practitioner then may insert the electrical stimulation lead 200 through the external component 221 of the introducer 219, advancing the electrical stimulation lead 200 through connective tissue 114 to the final lead location 150 proximate the stimulation locus (+). The final lead location 150 may be at or proximate the stimulation locus (+). As shown in FIG. 19, the medical practitioner then may remove the external component 221 of the introducer 219 from the subject. Further the inventive methods include a method for treating a tibial nerve-related condition or disease in a subject having a tibial nerve-related condition or disease. These methods may include depositing an electrical stimulation lead 200 at the tibial nerve 122 in a subject as described above, obtaining a controller module 204 and activating the controller module 204 to cause the electrical stimulation lead 200 to emit an electrical pulse to the tibial nerve 122 of the subject, thereby modulating the tibial nerve 122 and treating the tibial nerve-related condition or disease in the subject. In one aspect, the controller module 204 is in wireless communication with the electrical stimulation lead 200.

There are two anatomical locations that will accommodate the retrograde movement of the electrical stimulation lead 200 and also will place the electrical stimulation lead 200 in correct proximity and orientation for stimulation of tibial nerve 122. The first location, as described above, is within the space or safe zone 126. The connective tissue 114 in space or safe zone 126 will provide the purchase and fixation substrate for a flanged, tined, or other design of an electrical stimulation lead 200 to prevent lead migration.

The intravascular space of the posterior tibial vein (part of tibial vascular bundle 124) is the second anatomical location that will accommodate retrograde placement of an electrical stimulation lead 200 and provide for placement of the electrical stimulation lead 200 substantially parallel to the tibial nerve 122. The tibial vascular bundle 124 includes the posterior tibial vein. On the plantar aspect of the foot, medial and lateral plantar veins arise. These veins combine to form the posterior tibial and fibular veins. The posterior tibial vein accompanies the posterior tibial artery, entering the leg posteriorly to the medial malleolus. By placing electrical stimulation lead 200 percutaneously into the vein, similar to starting an intravenous (IV) access, the lead will by definition lie parallel to and in proximity to the tibial nerve. The posterior tibial vein is behind the medial malleolus 106 and is available for access at this location. Also, ultrasound can help identify the vein. In another embodiment, a small incision is made to help identify the vein for IV lead access. The intravenous space does not have the substrate of connective tissue for a flanged or tined lead to "grab". As such, an alternate lead design would be required for lead placement at this location, e.g., a stent, coil, or other intravenous-friendly configuration.

There are several advantages of retrograde lead placement. First, the inventive methods allow for advancement of the electrical stimulation lead 200 from an area distal to the tibial nerve 122 and to an area more proximal thereto, and along the tibial nerve 122, with the advantage of having a more robust region of the tibial nerve 122 to stimulate and result in enhanced afferent stimulation to the spinal cord and brain (not shown). This is a safe and stable area for lead placement.

With the inventive methods, the electrical stimulation lead 200 may have electrodes toward the distal end 203 of the electrical stimulation lead 200 and circuitry and an antenna toward the proximal end. The retrograde approach results in the circuitry and an antenna being at the level of the ankle (rather than the midcalf, as with an ante-grade approach). From a subject comfort standpoint, the antenna of the electrical stimulation lead 200 can be positioned around the ankle or within the sock to be in line of sight of the receiver rather than at the mid-calf. This will allow for better connectivity and will result in a more stable region for the antenna. Finally, the retrograde approach will result in the electrical stimulation lead 200 being parallel to the tibial nerve 122, will avoid penetrating lower leg muscles, and the electrical stimulation lead 200 will be stable with ambulation.

Further, the inventive methods have the advantage in that the electrodes of the electrical stimulation lead 200 are proximate the tibial nerve allowing for configuration of different stimulation parameters based on different combinations of electrode use. This proximity allows for lower stimulation voltages that can improve clinical efficacy; and for implanted power source devices; this prolongs battery life.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A method for depositing an electrical stimulation lead at a tibial nerve in a subject,
   wherein the subject includes a lower leg, a knee, a foot, the tibial nerve of the lower leg, skin of the lower leg, an outside surface of the skin of the lower leg, a tibia of the lower leg, an ankle interconnecting the tibia and the foot, a medial malleolus of the ankle of the lower leg, an Achilles tendon of the lower leg, and a tibial vascular bundle of the lower leg,
   wherein the tibia, the tibial nerve, and the tibial vascular bundle each have a length, and
   wherein the tibia, the tibial nerve and the tibial vascular bundle extend along a longitudinal axis from the ankle to the knee,
   the method comprising:
   determining an incision site that is between the medial malleolus and the Achilles tendon of the subject;
   making an incision through the skin of the lower leg at the incision site;
   locating a portion of the length of the tibial nerve in the subject;
   obtaining the electrical stimulation lead;
   inserting the electrical stimulation lead through the incision site and subcutaneously advancing the electrical stimulation lead in a direction from the incision site toward the knee of the subject, along the longitudinal axis, and substantially along the portion of the length of the tibial nerve; and
   depositing the electrical stimulation lead at a final lead location that is at the tibial nerve in the subject.

2. The method of claim 1, wherein a Tibialis Posterior, a Flexor Digitorum Longus, a Flexor Hallucis Longus, and a Soleus of the subject are located around the final lead location of the electrical stimulation lead.

3. The method of claim 1, wherein the determining step includes palpating an area between the medial malleolus and the Achilles tendon of the subject.

4. The method of claim 1, wherein the incision site is located about one-third of the distance from the medial malleolus to the Achilles tendon of the subject.

5. The method of claim 1, further comprising:
   obtaining an introducer, wherein the introducer has a distal end, and has a predetermined length that is at least as long as the electrical stimulation lead;
   inserting the distal end of the introducer through the incision site;

subcutaneously advancing the predetermined length of the introducer toward a stimulation locus on the portion of the length of the tibial nerve;

obtaining an electrical stimulation apparatus capable of emitting an electrical charge;

connecting the electrical stimulation apparatus to the proximal end of the inserted introducer;

activating the electrical stimulation apparatus to emit an electrical charge to the introducer; and determining that the distal end of the introducer is at or proximate the stimulation locus if the subject shows a physiological response to the electrical charge.

6. The method of claim 5, further comprising:

inserting the electrical stimulation lead through the introducer;

advancing the electrical stimulation lead through the introducer and to the final lead location, wherein the final lead location is at or proximate the stimulation locus; and removing the introducer from the subject.

7. The method of claim 1, wherein the step of locating the portion of the length of the tibial nerve includes determining a location of a portion of the length of the tibial vascular bundle, wherein the location of the portion of the length of the tibial vascular bundle is a proxy for the location of the portion of the length of the tibial nerve.

8. The method of claim 7, wherein blood flow through the tibial vascular bundle is indicative of the location of the portion of the length of the tibial vascular bundle.

9. The method of claim 1, wherein the electrical stimulation lead has a proximal end and a distal end and a longitudinal dimension from its proximal end to its distal end.

10. The method of claim 9, wherein, at the final lead location, the longitudinal dimension of the electrical stimulation lead is oriented substantially parallel to the portion of the length of the tibial nerve.

11. The method of claim 9, wherein the locating the portion of the length of the tibial nerve step includes locating a portion of the length of the tibia of the subject and marking a plurality of locations along the portion of the length of the tibia by placing a plurality of marks on the outside surface of the skin of the lower leg, at the tibia of the subject, and spaced-apart along the longitudinal axis of the tibia, and wherein the location of the plurality of marks is a proxy for the location of the portion of the length of the tibial nerve.

12. The method of claim 11, wherein the electrical stimulation lead is connected to a housing having a proximal end and distal end and having a longitudinal dimension from its proximal end to its distal end, wherein the longitudinal dimension of the housing is longer than the longitudinal dimension of the electrical stimulation lead, and wherein the electrical stimulation lead is located toward the distal end of the housing.

13. The method of claim 12, further comprising:

disconnecting the electrical stimulation lead from a portion of the housing to deposit the electrical stimulation lead at the final lead location;

removing the disconnected portion of the housing from the subject; and suturing shut the incision.

14. The method of claim 11, further comprising:

obtaining a finder needle, wherein the finder needle has cannula, proximal and distal ends, and a total length, and has a predetermined length that is at least as long as the longitudinal dimension of the electrical stimulation lead, that is less than the total length of the finder needle, and that extends from the distal end toward the proximal end of the finder needle;

wherein the locating the portion of the length of the tibial nerve step further includes inserting the distal end of the finder needle through the incision site;

subcutaneously advancing the predetermined length of the finder needle toward a stimulation locus on the portion of the length of the tibial nerve;

obtaining an electrical stimulation apparatus capable of emitting an electrical charge;

connecting the electrical stimulation apparatus to the proximal end of the inserted finder needle;

activating the electrical stimulation apparatus to emit an electrical charge to the finder needle; and determining that the distal end of the finder needle is at or proximate the stimulation locus if the subject shows a physiological response to the electrical charge.

15. The method of claim 14, wherein the predetermined length of the finder needle is about the length of the electrical stimulation lead.

16. The method of claim 14 wherein the physiological response is a motor-response in the foot or toe of the subject.

17. The method of claim 14, wherein it has been determined that the distal end of the finder needle is at or proximate the stimulation locus, the method further comprising:

obtaining a guide wire, wherein the guide wire has proximal and distal ends, has a total length, and has a predetermined length that is about the same as the predetermined length of the finder needle, that is less than the total length of the guide wire, and that extends from distal end of the guide wire toward its proximal end;

inserting the distal end of the guide wire through cannula of the finder needle;

advancing the predetermined length of the guide wire to the stimulation locus; and removing the finder needle from subject.

18. The method of claim 17, further comprising:

obtaining an introducer, wherein the introducer has proximal and distal ends, has a total length, and has a predetermined length that is about the same as the predetermined length of the finder needle, that is less than the total length of the introducer, and that extends from distal end of the introducer toward the proximal end of the introducer;

placing the distal end of the introducer over the proximal end of the guide wire;

advancing the predetermined length of the introducer to the stimulation locus; and removing the guide wire from subject.

19. The method of claim 18, further comprising:

inserting the distal end of the electrical stimulation lead through the introducer;

advancing the electrical stimulation lead to the final lead location, wherein the final lead location is at or proximate the stimulation locus; and removing the introducer from the subject.

20. A method for treating a tibial nerve-related condition or disease in a subject having the tibial nerve-related condition or disease:
 wherein the subject a lower leg, a knee, a foot, the tibial nerve of the lower leg, skin of the lower leg, an outside surface of the skin of the lower leg, a tibia of the lower leg, an ankle interconnecting the lower leg and the foot, a medial malleolus of the ankle of the lower leg, an Achilles tendon of the lower leg, and a tibial vascular bundle of the lower leg,
 wherein the tibia, the tibial nerve, and the tibial vascular bundle each have a length, and
 wherein the tibia, the tibial nerve and the tibial vascular bundle extend along a longitudinal axis from the ankle to the knee,
 the method comprising:
 determining an incision site that is between the medial malleolus and the Achilles tendon of the subject;
 making an incision through the skin of the lower leg at the incision site;
 locating a portion of the length of the tibial nerve in the subject;
 obtaining the electrical stimulation lead;
 inserting the electrical stimulation lead through the incision site and subcutaneously advancing the electrical stimulation lead in a direction from the incision site toward the knee of the subject, along the longitudinal axis, and substantially along the portion of the length of the tibial nerve;
 depositing the electrical stimulation lead at a final lead location that is at the tibial nerve in the subject;
 obtaining an controller module, wherein the controller module is in communicable relation with the electrical stimulation lead, and wherein the controller module is activatable to cause the electrical stimulation lead to emit an electrical pulse to the tibial nerve of the subject; and
 activating the controller module to cause the electrical stimulation lead to emit an electrical pulse to the tibial nerve, thereby modulating the tibial nerve and treating the tibial nerve-related condition or disease in the subject.

21. The method of claim 20, wherein the controller module is in wireless communication with the electrical stimulation lead.

22. The method of claim 20, wherein the tibial nerve-related condition or disease in the subject is selected from overactive bladder syndrome, urge incontinence, clitoral pain, peripheral neuropathy from dysfunction of the tibial nerve, colonic constipation, fecal or urinary incontinence, chronic pelvic pain syndrome, perineal or perianal pain, chronic prostatitis, stress incontinence, bladder pain, bladder inflammation, vesico-urethral dysfunction, genito-urinary disorders, urge frequency, urinary pain, erectile/sexual disorders, non-obstructive urinary retention, and interstitial cystitis/painful bladder syndrome.

* * * * *